United States Patent [19]
Montana et al.

[11] Patent Number: 6,100,266
[45] Date of Patent: Aug. 8, 2000

[54] HYDROXAMIC AND CARBOXYLIC ACID DERIVATIVES

[75] Inventors: John Gary Montana; Andrew Douglas Baxter; David Alan Owen, all of Cambridge, United Kingdom

[73] Assignee: Darwin Discovery Limited, United Kingdom

[21] Appl. No.: 09/239,603

[22] Filed: Jan. 29, 1999

[51] Int. Cl.$^7$ ...................... A61K 31/495; A61K 31/455; A61K 31/44; A61K 31/38

[52] U.S. Cl. .................. 514/255; 514/255; 514/317; 514/347; 514/424; 514/432; 514/451; 514/545; 514/570; 544/383; 546/221; 546/294; 548/550; 549/65; 549/419; 560/11; 562/429

[58] Field of Search ........................ 514/255, 545, 514/570, 317, 347, 432, 424, 451; 544/383; 560/11; 562/429; 548/550; 546/221, 294; 549/65, 419

[56] References Cited

U.S. PATENT DOCUMENTS

| | | | |
|---|---|---|---|
| 5,847,153 | 12/1998 | Warpehoski et al. | 548/319.5 |
| 5,872,152 | 2/1999 | Brown et al. | 514/575 |
| 5,962,481 | 10/1999 | Levin et al. | 514/352 |
| 5,985,900 | 11/1999 | Bender et al. | 514/336 |

FOREIGN PATENT DOCUMENTS

| | | |
|---|---|---|
| 9635714 | 11/1996 | WIPO . |
| 9839316 | 9/1998 | WIPO . |

OTHER PUBLICATIONS

Hattori, Koichi, Takao Hirano, Chifuyu Ushiyama et al. (1997) "A Metalloproteinase Inhibitor Prevents Lethal Acute Graft–Versus–Host Disease in Mice" *Blood* 90(2):542–548.

Witte, Maria B., Frank J. Thornton, Teruo Kiyama et al. (1998) "Metalloproteinase inhibitors and wound healing: A novel enhancer of wound strength" *Surgery* 124(2):464–470.

Boeykens, M., Norbert De Kimpe, Kourosch Abbaspour Tehrani (1994) "Synthesis of 1–Amino–2,2–dialkylcyclopropanecarboxylic Acids via Base–Induced Cyclization of γ–Chloro–α–imino Esters" J. Org. Chem. 59:6973–6985.

Johnson, Peter Y., Mark Berman (1975) "The Photochemical Reactions of 1–Thiacycloheptan–4–one Derivatives: An Approach to Pantothiolactone" J. Org. Chem. 40(21):3046–3057.

Kukolja, S. and Lj. Polak (1962) "Sulphur–Containing Pantothenic Acid Derivatives" Croatica Chemica Acta 34:199–202.

Nicolet, Ben H. (1935) "The Addition of Mercaptans to Certain Double Bonds" The Research Laboratories of the Bureau of Dairy Industry, United States Department of Agriculture 57:1098–1099.

*Primary Examiner*—Peter O'Sullivan
*Attorney, Agent, or Firm*—Saliwanchik, Lloyd & Saliwanchik

[57] ABSTRACT

For the treatment of cancer, inflammation, and other conditions associated with matrix metalloproteinases or that are mediated by TNFα or enzymes involved in the shedding of L-selectin, CD23, the TNF receptors, IL-1 receptors, or IL-6 receptors, disclosed are compounds of the general formula

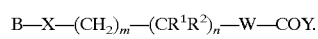

$$B-X-(CH_2)_m-(CR^1R^2)_n-W-COY.$$

15 Claims, No Drawings

HYDROXAMIC AND CARBOXYLIC ACID DERIVATIVES

FIELD OF THE INVENTION

This invention relates to novel compounds including hydroxamic and carboxylic acid derivatives, and to their use in medicine.

BACKGROUND TO THE INVENTION

Metalloproteinases, including matrix metalloproteinase (MMP), (human fibroblast) collagenase, gelatinase and TNF convertase (TACE), and their modes of action, and also inhibitors thereof and their clinical effects, are described in WO-A-9611209, WO-A-9712902 and WO-A-9719075, the contents of which are incorporated herein by reference. MMP inhibitors may also be useful in the inhibition of other mammalian metalloproteinases such as the adamalysin family (or ADAMs) whose members include TNF convertase (TACE) and ADAM-10, which can cause the release of TNFα from cells, and others, which have been demonstrated to be expressed by human articular cartilage cells and also involved in the destruction of myelin basic protein, a phenomenon associated with multiple sclerosis.

Compounds which have the property of inhibiting the action of metalloproteinases involved in connective tissue breakdown, such as collagenase, stromelysin and gelatinase, have been shown to inhibit the release of TNF both in vitro and in vivo. See Gearing et al (1994), Nature 370:555–557; McGeehan et al (1994), Nature 370:558–561; GB-A-2268934; and WO-A-9320047. All of these reported inhibitors contain a hydroxamic acid zinc-binding group, as do the imidazole-substituted compounds disclosed in WO-A-9523790. Other compounds that inhibit MMP and/or TNF are described in WO-A-9513289, WO-A-9611209, WO-A-96035687, WO-A-96035711, WO-A-96035712 and WO-A-96035714.

WO-A-9839316 (which may be prior art under Article 54(3) EPC) discloses compounds of formula I (below) of the type where W is CHOH and B is aryl, heteroaryl, cycloalkyl or heterocycloalkyl bonded through carbon to X.

SUMMARY OF THE INVENTION

The invention encompasses compounds of formula (I), many of which are novel, which are useful inhibitors of matrix metalloproteinases and/or TNFα-mediated diseases, including degenerative diseases and certain cancers.

Compounds according to the invention are of the general type represented by formula (I):

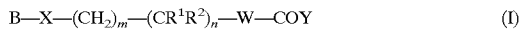

$$B-X-(CH_2)_m-(CR^1R^2)_n-W-COY \quad (I)$$

wherein $m=0-2$;

$n=1-2$, provided than when $m=0$ then $n=2$;

X is $S(O)_{0-2}$;

Y is H, OH or NHOH;

W is C=O or CHOH, or when Y is H, W may additionally be N—OR$^8$;

$R^1$ is H or a group (optionally substituted with $R^7$) selected from $C_{1-6}$ alkyl, $C_{2-6}$ alkenyl, aryl, $C_{1-6}$ alkyl-aryl, heteroaryl, $C_{1-6}$ alkyl-heteroaryl, heterocycloalkyl, $C_{1-6}$ alkyl-heterocycloalkyl, cycloalkyl and $C_{1-6}$ alkyl-cycloalkyl; and $R^2$ is H or $C_{1-6}$ alkyl, provided that $(CR^1R^2)_n$ is not $(CH_2)_n$;

or $CR^1R^2$ is a cycloalkyl or heterocycloalkyl ring optionally substituted with $R^7$ or a group (optionally substituted with $R^7$) selected from $C_{1-6}$ alkyl, aryl, $C_{1-6}$ alkyl-aryl, heteroaryl and $C_{1-6}$ alkyl-heteroaryl;

B is $C_{1-6}$ alkyl-aryl, $C_{1-6}$ alkyl, cycloalkyl, $C_{1-6}$ alkyl-cycloalkyl, cycloalkenyl, heterocycloalkenyl, $C_{1-6}$ alkyl-heteroaryl, heterocycloalkyl, $C_{1-6}$ alkyl-heterocycloalkyl, aryl or heteroaryl, any of which groups is optionally substituted by a substituent selected from $R^3$, $C_{1-6}$ alkyl-$R^3$, $C_{2-6}$ alkenyl-$R^3$, aryl (optionally substituted with $R^3$), aryl-$C_{1-6}$ alkyl-$R^3$, $C_{1-6}$ alkyl-aryl (optionally substituted with $R^3$), $C_{1-6}$ alkyl-heteroaryl (optionally substituted with $R^3$), aryl-$C_{2-6}$ alkenyl-$R^5$, heteroaryl (optionally substituted with $R^3$), heteroaryl-$C_{1-6}$ alkyl-$R^3$, cycloalkyl (optionally substituted with $R^3$), or heterocycloalkyl (optionally substituted with $R^3$);

$R^3$ is $C_{1-6}$ alkyl, halogen, CN, $NO_2$, $N(R^4)_2$, $OR^4$, $COR^4$, $C(=NOR^6)R^4$, $CO_2R^8$, $CON(R^4)_2$, $NR^4R^5$, $S(O)_{0-2}R^6$ or $SO_2N(R^4)_2$;

$R^4$ is H or a group selected from $C_{1-6}$ alkyl, aryl, $C_{1-6}$ alkyl-aryl, heteroaryl, $C_{1-6}$ alkyl-heteroaryl, cycloalkyl, $C_{1-6}$ alkyl-cycloalkyl, heterocycloalkyl and $C_{1-6}$ alkyl-heterocycloalkyl, wherein said group is optionally substituted with $R^6$, $COR^6$, $SO_{0-2}R^6$, $CO_2R^6$, $OR^6$, $CONR^8R^6$, $NR^8R^6$, halogen, CN, $SO_2NR^8R^6$ or $NO_2$, and for each case of $N(R^4)_2$ the $R^4$ groups are the same or different or $N(R^4)_2$ is heterocycloalkyl optionally substituted with $R^6$, $COR^6$, $SO_{0-2}R^6$, $CO_2R^6$, $OR^6$, $CONR^8R^6$, $NR^8R^6$, halogen, CN, $SO_2NR^8R^6$ or $NO_2$;

$R^5$ is $COR^4$, $CON(R^4)_2$, $CO_2R^6$ or $SO_2R^6$;

$R^6$ is $C_{1-6}$ alkyl, aryl, $C_{1-6}$ alkyl-aryl, heteroaryl or $C_{1-6}$ alkyl-heteroaryl;

$R^7$ is $OR^4$, $COR^4$, $CO_2R^8$, $CON(R^4)_2$, $NR^4R^5$, $S(O)_{0-2}R^6$, $SO_2N(R^4)_2$, halogen, CN or cycloimidyl (optionally substituted with $R^8$); and $R^8$ is H or $C_{1-6}$ alkyl;

and the salts, solvates, hydrates, N-oxides, protected amino, protected carboxy and protected hydroxamic acid derivatives thereof.

Combinations of substituents and/or variables are only permissible if such combinations result in stable compounds.

DESCRIPTION OF THE INVENTION

Preferred compounds of the invention are those wherein any one or more of the following apply:

X is $SO_2$;

$R^1$ is optionally substituted $C_{1-6}$ alkyl, $C_{1-6}$ alkyl-heteroaryl, or $C_{1-6}$ alkyl-heterocycloalkyl; or $CR^1R^2$ forms the said optionally substituted ring;

B is cycloalkyl, heterocycloalkyl, aryl or heteroaryl any of which groups is optionally substituted by a substituent selected from $R^3$, aryl (optionally substituted with $R^3$) and heteroaryl (optionally substituted with $R^3$);

$R^3$ is $OR^4$ or $COR^4$;

$R^4$ is optionally substituted aryl, $C_{1-6}$ alkyl-aryl, heteroaryl or $C_{1-6}$ alkyl-heteroaryl; and $R^7$ is $CO_2R^8$, $CON(R^4)_2$, $NR^4R^5$, $S(O)_{0-2}R^6$, $SO_2N(R^4)_2$ or optionally substituted cycloimidyl.

The compounds of the Examples are particularly preferred.

It will be appreciated that the compounds according to the invention can contain one or more asymmetrically substituted carbon atoms. The presence of one or more of these asymmetric centres in a compound of formula (I) can give rise to stereoisomers, and in each case the invention is to be understood to extend to all such stereoisomers, including enantiomers and diastereomers, and mixtures including racemic mixtures thereof.

It will further be appreciated that the compounds according to the invention may contain an oxime. This oxime can give rise to geometrical isomers, and in each case the invention is to be understood to extend to all such isomers and mixtures thereof.

As used in this specification, alone or in combination, the term "$C_{1-6}$ alkyl" refers to straight or branched chain alkyl moiety having from one to six carbon atoms, including for example, methyl, ethyl, propyl, isopropyl, butyl, tert-butyl, pentyl, hexyl and the like.

The term "$C_{2-6}$ alkenyl" refers to a straight or branched chain alkyl moiety having two to six carbon atoms and having in addition one double bond, of either E or Z stereochemistry where applicable. This term would include for example, vinyl, 1-propenyl, 1- and 2-butenyl, 2-methyl-2-propenyl etc.

The term "cycloalkyl" refers to a saturated alicyclic moiety having from three to six carbon atoms and which is optionally benzofused at any available position. This term includes for example cyclopropyl, cyclobutyl, cyclopentyl, cyclohexyl, indanyl and tetrahydronaphthyl.

The term "heterocycloalkyl" refers to a saturated heterocyclic moiety having from three to six carbon atoms and one or more heteroatoms selected from N, O, S and oxidised versions thereof, and which is optionally benzofused at any available position. This term includes, for example, azetidinyl, pyrrolidinyl, tetrahydrofuranyl, piperidinyl, indolinyl and tetrahydroquinolinyl.

The term "cycloalkenyl" refers to an alicyclic moiety having from three to six carbon atoms and having in addition one double bond. This term includes, for example, cyclopentenyl and cyclohexenyl.

The term "heterocycloalkenyl" refers to an alicyclic moiety having three to six carbon atoms and one or more heteroatoms selected from N, O, S and oxidised versions thereof, and having in addition one double bond. This term includes, for example, dihydropyranyl.

The term "aryl" refers to an aromatic carbocyclic radical having a single ring or two condensed rings. This term includes, for example phenyl or naphthyl.

The term "heteroaryl" refers to aromatic ring systems of five to ten atoms of which at least one atom is selected from O, N and S, and includes, for example, furanyl, thiophenyl, pyridyl, indolyl, quinolyl and the like.

The term "cycloimidyl" refers to a saturated ring of five to ten atoms containing the atom sequence —C(=O)NC(=O)—. The ring may be optionally benzofused at any available position. Examples include succinimidoyl, phthalimidoyl and hydantoinyl.

The term "benzofused" refers to the addition of a benzene ring sharing a common bond with the defined ring system.

The term "optionally substituted" means optionally substituted with one or more of the groups specified, at any available position or positions.

The term "halogen" means fluorine, chlorine, bromine or iodine.

The terms "protected amino", "protected carboxy" and "protected hydroxamic acid" mean amino, carboxy and hydroxamic acid groups which can be protected in a manner familiar to those skilled in the art. For example, an amino group can be protected by a benzyloxycarbonyl, tert-butoxycarbonyl, acetyl or like group, or may be in the form of a phthalimido or like group. A carboxyl group can be protected in the form of an ester such as the methyl, ethyl, benzyl or tert-butyl easter. A hydroxamic acid may be protected as either N or O-substituted derivatives, such as O-benzyl or O-tert-butyldimethylsilyl.

Salts of compounds of formula (I) include pharmaceutically-acceptable salts, for example acid addition salts derived from inorganic or organic acids, such as hydrochlorides, hydrobromides, p-toluenesulphonates, phosphates, sulphates, perchlorates, acetates, trifluoroacetates, propionates, citrates, malonates, succinates, lactates, oxalates, tartrates and benzoates.

Salts may also be formed with bases. Such salts include salts derived from inorganic or organic bases, for example alkali metal salts such as magnesium or calcium salts, and organic amine salts such as morpholine, piperidine, dimethylamine or diethylamine salts.

When the "protected carboxy" group in compounds of the invention is an esterified carboxyl group, it may be a metabolically-labile ester of formula $CO_2R^9$ where $R^9$ may be an ethyl, benzyl, phenethyl, phenylpropyl, α- or β-naphthyl, 2,4-dimethylphenyl, 4-tert-butylphenyl, 2,2,2-trifluoroethyl, 1-(benzyloxy)benzyl, 1-(benzyloxy)ethyl, 2-methyl-1-propionyloxypropyl, 2,4,6-trimethylbenzyloxymethyl or pivaloylmethyl group.

Compounds of the general formula (I) may be prepared by any suitable method known in the art and/or by the following processes.

It will be appreciated that, were a particular stereoisomer of formula (I) is required, the synthetic processes described herein may be used with the appropriate homochiral starting material and/or isomers maybe resolved from mixtures using conventional separation techniques (e.g. HPLC).

The compounds according to the invention may be prepared by the following process. In the description and formulae below the groups $R^1$, $R^2$, $R^3$, $R^4$, $R^5$, $R^6$, $R^7$, $R^8$, $R^9$, B, W, X and Y are as defined above, except where otherwise indicated. It will be appreciated that functional groups, such as amino, hydroxyl or carboxyl groups, present in the various compounds described below, and which it is desired to retain, may need to be in protected from before any reaction is initiated. In such instances, removal of the protecting group may be the final step in a particular reaction. Suitable protecting groups for such functionality will be apparent to those skilled in the art. For specific details see Greene et al, "Protective Groups in Organic Synthesis", Wiley Interscience.

Compound of formula (I) where W is CHOH and Y is OH may be prepared by the hydrolysis of compounds of formula B—X—$(CH_2)_m$—$(CR^1R^2)_n$—CHOH—CN (II) by, for example, treatment with inorganic acid such as 7 M HCl at an appropriate temperature, such as 80° C.

Compounds of formula (II) may be prepared by reaction of an aldehyde of formula B—X—$(CH_2)_m$—$(CR^1R^2)_n$—CHO (III) with an inorganic cyanide, such as potassium cyanide in an appropriate solvent, such as aqueous $NaHSO_3$.

Compounds of formula (III) may be prepared by reduction of an ester of formula formula B—X—$(CH_2)_m$—$(CR^1R^2)_n$—$CO_2R^{10}$ (IV) where $R^{10}$ represents a suitable group such as methyl or ethyl, by treatment with a reducing agent, such as diisobutylaluminium hydride, in appropriate solvent, such as toluene.

Compounds of formula (IV) where X=S are readily prepared by alkylation of a compound B—SH with an alkylating agent of the form $Z\text{-}(CH_2)_m\text{—}(CR_1R_2)_n\text{—}CO_2R^{10}$ (V), where Z is a leaving group (e.g. a halogen such as bromine, or an alkylsulfonate easter such as methanesulfonate). Many compounds of formula (V) are B—SH are available commercially, or may be prepared by standard chemistry known to those skilled in the art from materials available commercially.

Compounds of formula (I) where W is C=O and Y is OH may also be prepared from compounds of formula (IV) where $R^{10}$=H by a three step sequence involving (i) reaction with cyanomethylene-triphenylphosphorane, (ii) oxidation with ozone, and (iii) aqueous hydrolysis, as described in *Tetrahedron Lett.*, 1992, 33, 6003 and *J. Org. Chem.*, 1994, 59, 4364.

Compounds of formula (IV) where m=1, n=1 and $R^2$=H may also be prepared by the reaction of a compound B—SH with an acrylate of the form $H_2CCR^1CO_2H$ (VI). Compounds (VI) may be prepared by the Mannich reaction (i.e. with paraformaldehyde and piperidine in a suitable organic solvent, such as 1,4-dioxane) on a dicarboxylic acid of general formula $HO_2C\text{—}CHR^1\text{—}CO_2H$ (VII). This reaction involves an eliminative decarboxylation step resulting in the formation of an α,β-unsaturated carboxylic acid directly.

Dicarboxylic acids of formula (VII) may be prepared by the alkylation of, for instance, diethyl malonate with an alkylating agent of formula $R^1$-Z (VIII), wherein Z is as defined above, followed by hydrolysis under basic conditions. Many alkylating agents of general formula (VIII) are available commercially or may be prepared from materials available commercially by methods known to those skilled in the art.

Compounds of formula (I) where Y is H and W is N—$OR^8$ may be prepared by N-formulation of a compound of formula B—X—$(CH_2)_m$-$(CR^1R^2)_n$—$NHOR^8$ (IX). Compounds of formula (IX) where m=1, n=1 and X=$SO_2$ may be prepared by the addition of $R^8ONH_2$ to a vinyl sulfone of formula B—$SO_2CHCR^1R^2$ (X). This reaction may be performed in a suitable organic solvent, such as tetrahydrofuran, in the presence of an organic base, such as triethylamine. Compounds of formula (X) may be prepared by the condensation of a sulfone of formula B—$SO_2$—$CH_3$ (XI) with a ketone of formula $R_1COR_2$ (XII). Suitable conditions for this reaction are an appropriate base, such as sodium hydride, in an inert solvent, such as THF. Many sulfones (XI) and ketones (XII) are known, or may be prepared readily by methods known to those skilled in the art.

Compounds of formula (IX) may be prepared alternatively by N-oxidation of an amine of formula B—X—$(C_2)_m CR^1R^2)_n NH_2$ (XIII) in a three step process involving (i) reaction of the free amine with an aldehyde to give an appropriate imine, (ii) reaction of the imine with an oxidising agent such as meta-chloroperbenzoic acid to give the corresponding oxaziridine, and (iii) cleavage of the oxaziridine with a hydroxylamine to give the target hydroxylamine of formula (IX) (for example, see *Synthesis*, 1987, 1115).

Amines of formula (XIII) may be prepared by either (when X is $SO_2$ and B is lined through nitrogen to X) reaction of B with an acylating agent of formula Z-$SO_2$—$(CH_2)_m(CR^1R^2)_nNHR^{11}$ (XIX), or (when X is S and B is linked through carbon to X) reaction of a sulfanyl compound of formula B—SH with a alkylating agent of formula $Z\text{-}(CH_2)_m(CR^1R^2)_nNHR^{11}$ (XX), wherein $R^{11}$ is a suitable amine protecting group (see Greene et al, "Protecting Groups in Organic Synthesis", Wiley Interscience) which may be removed after these transformations. Compounds of formula (XIX) may in turn be prepared from compounds of formula (XX) by reaction with a compound of formula Q-SH, where Q is a suitable labile group such as acetyl, followed by reaction with, for example, chlorine and water, to give a compound of formula (XIX) where Z is Cl.

Compounds of formula (XX) are available commercially or may be prepared from materials available commercially by methods known to those skilled in the art. For example, compounds (XX) where m=1 and n=1 may be prepared from amino acids of formula $HO_2CCR^1R^2NHR^{11}$ (XXI) by a two-step sequence involving (i) reduction of the acid to a primary alcohol of formula $HOCH_2CR^1R^2NHR^{11}$ (XXII) with a suitable reagent such as borane in an inert solvent, and (ii) conversion of the primary alcohol to a leaving group for example by reaction with methanesulfonyl chloride in the presence of an organic base such as triethylamine in an inert solvent, to give a compound of formula (XX) where Z is methanesulfonate. Compounds of formula (XXI) are known, or may be prepared by known methods.

Compounds of formula (I) or any appropriate intermediate may also be prepared by interconversion of compounds of the same formula. Thus, for example, a compound of formula (I) wherein $R^1$ is a $C_{1-6}$ alkyl group may be prepared by hydrogenation (using palladium on carbon in suitable solvent, such as an alcohol, e.g. ethanol) of a compound of formula (I) wherein $R^1$ is a $C_{2-6}$ alkenyl group. A compound of formula (I) where W is C=O may be prepared from a compound where W is CHOH by oxidation with, for example oxalyl chloride and dimethyl sulfoxide in the presence of an organic base such as triethylamine. Compounds of formula (I) where Y=NHOH may be prepared from a compound where Y=OH using standard chemistry, known to those skilled in the art, optionally via the intermediate preparation of hydroxamides $NHOR^{12}$ where $R^{12}$ is a suitable protecting group such as benzyl, tert-butyl or tert-butyldimethylsilyl (TBDMS).

Similarly, a compound of formula (I), (IV), (IX), (XIII), (XIX) or any other appropriate intermediate, where X=$SO_2$ may be prepared from a corresponding compound where X=S by oxidation with, for example Oxone® in appropriate solvent, such as methanol-water.

Any mixtures of final products or intermediates obtained can be separated on the basis of the physico-chemical differences of the constituents, in known manner, into the pure final products or intermediates, for example by chromatography, distillation, fractional crystallization, or by formation of a salt if appropriate or possible under the circumstances.

The compounds according to the invention exhibit in vitro inhibiting activities with respect to the stromelysins, collagenases and gelatinases. Compounds according to the invention may also exhibit in vitro inhibition of membrane shedding events known to be mediated by metalloproteinases, for example, α-APP, ACE, TGF-α, TNF-α, Fas ligand, TNFR-I, TNFR-II, CD30, Il-6R, CD43, CD44, CD16-I, CD16-II, Folate receptor, CD23, or IL-1RII.

The activity and selectivity of the compounds may be determined by use of the appropriate enzyme inhibition test, for example as described in Examples A–M of WO-A-9805635, by the assay for the inhibition of CD23 shedding described in PCT/GB98/03395, or by the following assay of TNF RI shedding.

The potency of the compounds of general formula (I) to act as inhibitors of the production of TNF RI is determined using the following procedure. A 100 μM solution of the inhibitor being tested or dilutions thereof is incubated at 37° C. in an atmosphere of 5% $CO_2$ with peripheral blood mononuclear cells (PBMC). PBMC are isolated from buffy coats by standard procedures using Ficoll. A 100 μM solution of the inhibitor being tested or dilutions thereof is incubated for 22 hours at 37° C. in an atmosphere of 5% $CO_2$ with $1 \times 10^6$/ml PBMC stimulated with LPS. The cells are centrifuged down and the supernatant is assayed for TNF RI using a commercially available ELISA kit (R & D Systems). The activity in the presence of 0.1 mM inhibitor or dilutions thereof is compared to activity in a control devoid of inhibitor and results reported as that inhibitor concentration effecting 50% inhibition of the production of TNF RI.

This invention also relates to a method of treatment for patients (including man and/or mammalian animals raised in the dairy, meat or fur industries or as pets) suffering from disorders or diseases which can be attributed to stromelysin as previously described, and more specifically, a method of treatment involving the administration of the matrix metalloproteinase inhibitors of formula (I) as the active constituents.

Accordingly, the compounds of formula (I) can be used among other things in the treatment of osteoarthritis and rheumatoid arthritis, and in diseases and indications resulting from the over-expression of these matrix metalloproteinases such as found in certain metastatic tumour cell lines.

As mentioned above, compounds of formula (I) are useful in human or veterinary medicine since they are active as inhibitors of TNF and MMPs. Accordingly in another aspect, this invention concerns:

- a method of management (by which is meant treatment of prophylaxis) of disease or conditions mediated by TNF and/or MMPs in mammals, in particular in humans, which method comprises administering to the mammal an effective, amount of a compound of formula (I) above, or a pharmaceutically acceptable salt thereof; and
- a compound of formula (I) for use in human or veterinary medicine, particularly in the management (by which is meant treatment or prophylaxis) of diseases or conditions mediate by TNF and/or MMPs; and
- the use of a compound of formula (I) in the preparation of an agent for the management (by which is meant treatment or prophylaxis) of diseases or conditions mediated by TNF and/or MMPs.

The disease or conditions referred to above include inflammatory diseases, autoimmune diseases, cancer, cardiovascular diseases, diseases involving tissue breakdown such as rheumatoid arthritis, osteoarthritis, osteoporosis, neurodegeneration, Alzheimer's disease, stroke, vasculitis, Crohn's disease, ulcerative colitis, multiple sclerosis, periodontitis, gingivitis and those involving tissue breakdown such as bone resorption, haemorrhage, coagulation, acute phase response, cachexia and anorexia, acute infections, HIV infections, fever, shock states, graft versus host reactions, dermatological conditions, surgical wound healing, psoriasis, atopic dermatitis, epidermolysis bullosa, tumour growth, angiogenesis and invasion by secondary metastases, ophthalmological disease, retinopathy, corneal ulceration, reperfusion injury, migraine, meningitis, asthma, rhinitis, allergic conjunctivitis, eczema, anaphylaxis, restenosis, congestive heart failure, endometriosis, atherosclerosis, endosclerosis and aspirin-independent anti-thrombosis.

Compounds of formula (I) may also be useful in the treatment of pelvic inflammatory diseases (PID), age-related macular degeneration and cancer-induced bone resorption. Further, they can be used in the treatment of lung diseases, e.g. selected from cystic fibrosis, adult respiratory distress syndrome (ARDS), emphysema, bronchitis obliterans-organising pneumonia (BOOP), idiopathic pulmonary fibrosis (PIF), diffuse alveolar damage, pulmonary Langerhan's cell granulamatosis, pulmonary lymphangioleiomyomatosis (LAM) and chronic obstructive pulmonary disease (COPD).

For the treatment of rheumatoid arthritis, osteoarthritis, and in diseases and indications resulting from the over-expression of matrix metalloendoproteinases such as found in certain metastatic tumour cell lines or other diseases mediated by the matrix metalloendoproteinases or increased TNF production, the compounds of formula (I) may be administered orally, topically, parenterally, by inhalation spray or rectally in dosage unit formulations containing non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats etc, the compounds of the invention are effective in the treatment of humans.

The pharmaceutical composition containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tables contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874, to form osmotic therapeutic tablets for control release.

Formulations for oral use may also be presented as hard gelatin capsules where in the active ingredient is mixed with an inert solid diluent, for example calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate polyvinyl-pyrrolidone, gum tragacanth and gum acacia; dispersing or wetting agents may be a naturally occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such a polyoxyethylene with partial esters derived from fatty acids and hexitol anhydrides, for example polyoxyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent an done or more preservatives. Suitable dispersing or wetting agents and suspending agents are exemplified, for example sweetening, flavouring and colouring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be in a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc containing the compounds of Formula (I) are employed. For the purposes of this specification, topical application includes mouth washes and gargles.

Dosage levels of the order of from about 0.05 mg to about 140 mg per kilogram of body weight per day are useful in the treatment of the above-indicated conditions (about 2.5 mg to about 7 g per patient per day). For example, inflammation may be effectively treated by the administration of from about 0.01 to 50 mg of the compound per kilogram of body weight per day (about 0.5 mg to about 3.5 mg per patient per day).

The amount of active ingredient that may be combined with the carrier materials to produce a single dosage form will vary depending upon the host treated and the particular mode of administration. For example, a formulation intended for the oral administration of humans may vary from about 5 to about 95% of the total composition. Dosage unit forms will generally contain between from about 1 mg to about 500 mg of active ingredient.

It will be understood, however, that the specific dose level for any particular patient will depend upon a variety of factors including the activity of the specific compound employed, the age, body weight, general health, sex, diet time of administration, route of administration, rate of excretion, drug combination and the severity of the particular disease undergoing therapy.

The following Examples illustrate the invention. The following abbreviations apply: DMF is dimethylformamide; RT is room temperature; THF is tetrahydrofuran.

INTERMEDIATE 1

2-[(4-Methoxybenzenesulfonyl)methyl]-5-phenylpentanoic Acid

Was prepared according to the procedure described WO-A-9805635, as a colourless solid (2.5 g).

INTERMEDIATE 2

Methyl 2-[(4-Methoxybenzenesulfonyl)methyl]-5-phenylpentanoate

Employing a diazomethane kit, the reaction vessel was charged with potassium hydroxide (2.50 g), ethanol (5 ml) and water (4 ml), and the mixture heated in a water bath held at 65–75° C. Diazald (2.50 g), as a solution in diethyl ether (25 ml), was added dropwise to the reaction vessel (with caution), and the distillate collected in a trap cooled with carbon dioxide/acetone. Once the addition was complete, the diazald addition flask was rinsed into the reaction vessel with diethyl ether (2×1 ml), until the distillate was colourless. The pale yellow diazomethane solution thus collected was then added cautiously to a stirred, ice-cold solution of intermediate 1 (2.00 g) in tetrahydrofuran (25 ml). The mixture was then stirred in ice for one hour, after which time it was warmed to room temperature and purged with nitrogen until colourless. The solution was treated with a few drops of acetic acid to remove traces of diazomethane, and concentrated to dryness in vacuo to give the title compound (2.23 g, 100%) as a colourless oil.

TLC $R_f$ 0.67 (50% hexane/ethyl acetate with trace acetic acid).

INTERMEDIATE 3

2-[(4-Methoxybenzenesulfonyl)methyl]-5-phenylpentanal

Diisobutylaluminium hydride, as a 1.5 M toluene solution (7.5 ml), was added dropwise via syringe over ca. 45 minutes to a stirred solution of Intermediate 2 (2.82 g) in anhydrous toluene (30 ml), ensuring the temperature remained below −65° C. The mixture was maintained at this temperature for a further 45 minutes, after which time methanol (5 ml) was added dropwise, followed by 1 M hydrochloric acid (4 ml). After warming to room temperature, diethyl ether (25 ml) and 1 M hydrochloric acid (45 ml) were added, layers separated, and the aqueous phase extracted with diethyl ether (2×25 ml). The combined organic extracts were then washed with water (2×10 ml), brine (15 ml), dried (MgSO$_4$) and reduced in vacuo to leave a colourless oil (2.63 g). Purification by chromatography on silica, with 3% diethyl ether/dichloromethane as eluent provided the title compound (1.84 g, 71%) as a colourless oil.

TLC R$_f$ 0.47 (3% diethyl ether/dichloromethane), MS 364 (M+NH$_4^+$).

INTERMEDIATE 4

1-Cyano-2-[(4-methoxybenzenesulfonyl)methyl]-5-phenylpentanol

Intermediate 3 (1.724 g) was stirred vigorously with sodium metabisulfite (1.703 g) in water (10 ml) and ethanol (2 ml), and after 30 minutes, the suspension produced was treated with a solution of potassium cyanide (with caution) (0.486 g) in water (10 ml). After 2 hours, the mixture was extracted with diethyl ether (2×25 ml), and the combined extracts washed with water (20 ml), dried (MgSO$_4$), and reduced to give the title compound (1.463 g, 79%) as a colourless oil.

TLC R$_f$ 0.24 (3% diethyl ether/dichloromethane).

INTERMEDIATE 5

4-(4-Methoxybenzenesulfonylmethyl)-3-oxo-7-phenyl-2-(triphenylphosphanyl-idene)heptanenitrile To a stirred solution of Intermediate 1 (2.00 g), in dichloromethane (50 ml) and DMF (1 drop) at 0° C. was added oxalyl chloride (3.50 g). Stirring was continued for 15 mins at 0° C. and then for 45 mins at RT. The solvent was removed in vacuo. The residue was dissolved in dichloromethane (10 ml) and added to a solution of triphenylphosphoranylidene-acetonitrile (1.84 g) and bistrimethylacetamide (1.68 g) in dichloromethane (80 ml) at 0° C. under nitrogen. Stirring was continued for 10 mins at 0° C. and then at room temperature for 3 h. The reaction mixture was diluted with dichloromethane (100 ml) and washed with water (3×50 ml), sodium hydroxide solution (0.5 M; 50 ml), water (2×50 ml), brine (50 ml) and dried (MgSO$_4$). Filtration, evaporation of the solvent and purification of the residue by silica gel column chromatography, eluting with a mixture of 1:1 hexane/ethyl acetate containing a trace amount of acetic acid, gave the title compound (1.24 g, 35%) as a colourless foam.

TLC R$_f$ 0.32 (1:1 hexane/ethyl acetate, trace acetic acid).

INTERMEDIATE 6

Methanesulfonic Acid, 2S-tert-Butoxycarbonylamino-3-methyl-butyl Ester

L-Boc-Valinol (5 g) in dichloromethane (100 ml) was cooled in ice, and triethylamine (3.8 ml) and methanesulfonyl chloride (2.0 ml) were added dropwise. The cold solution was stirred for 2 h, then washed with water and brine, dried over MgSO$_4$ and evaporated to give the title compound (6.2 g, 95%) as colourless solid.

TLC R$_f$ 0.75 (ether).

INTERMEDIATE 7

Thioacetic Acid, S-(2S-tert-butoxycarbonylamino-3-methyl-butyl) Ester

A solution of Intermediate 6 (6.0 g) was stirred at room temperature in dimethylformamide (50 ml) with potassium thioacetate (4.0 g) for 18 h. The resulting thick suspension was diluted with water, extracted with ether (2×100 ml) and the solvent was washed with water, aqueous sodium bicarbonate solution and brine, then dried over MgSO$_4$ and evaporated to give the title compound (5.2 g, 88%) as beige solid.

TLC R$_f$ 0.43 (1:1 ether/hexanes).

INTERMEDIATE 8

(1S-Chlorosulfonylmethyl-2-methylpropyl)carbamic Acid, tert-Butyl Ester

Chlorine gas was bubbled through a solution of Intermediate 7 (2.0 g) in water (50 ml) and dichloromethane (50 ml) at 0° C. for 20 min, then the suspension was stirred vigorously for 20 min. The phases were separated and the organic layer was washed with iced water and brine, then dried over MgSO$_4$ and evaporated to give the title compound (2.20 g, 100%) as colourless solid.

TLC R$_f$ 0.35 (1:1 ether/hexanes).

INTERMEDIATE 9

{1S-[4-(4-Chlorophenyl)piperazine-1-sulfonylmethyl]-2-methylpropyl}carbamic Acid, tert-Butyl Ester A suspension of 4-chlorophenylpiperazine dihydrochloride (2.0 g) and triethylamine (3.3 ml) in dichloromethane (100 ml) was stirred for 10 minutes, then cooled in ice and a solution of Intermediate 8 was added dropwise. The mixture was stirred vigorously for 3 h, then washed with water, saturated aqueous sodium bicarbonate solution and brine. The organic layer was then dried over MgSO$_4$ and evaporated to give the title compound (2.50 g, 73%) as colourless crystalline solid.

TLC R$_f$ 0.63 (ether).

INTERMEDIATE 10

1S-[4-(4-Chlorophenyl)piperazine-1-sulfonylmethyl]-2-methylpropylamine

A solution of Intermediate 9 (2.50 g) in dichloromethane (60 ml) was treated with trifluoroacetic acid (30 ml), and the mixture was stirred for 2 h. The mixture was then evaporated to dryness and azeotroped with dichloromethane and hexanes. The residue was dissolved in water (100 ml) and the solution washed with ether. The aqueous layer was basified with 48% aqueous NaOH and the resulting suspension was extracted with EtOAc (3×100 ml). the solvent was washed with brine, dried over MgSO$_4$ and evaporated to give the title compound (1.85 g, 95%) as colourless solid.

TLC R$_b$ 0.15 (ether).

INTERMEDIATE 11

{1S-[4-(4-Chlorophenyl)piperazine-1-sulfonylmethyl]-2-methylpropyl}-(4-methoxybenzylidene)amine A solution of Intermediate 10 (1.8 g) and para-anisaldehyde (1.2 ml) in methanol (100 ml) was stirred with solid sodium carbonate (2 g) for 18 h at room temperature. The suspension was filtered and the filtrate evaporated and triturated with ethyl acetate (200 ml). The mixture was filtered and the filtrate evaporated to give the title compound (2.50 g, 100%) as a viscous pale yellow oil.

TLC $R_f$ 0.54 (ether/hexanes 1:2).

INTERMEDIATE 12

1-(4-Chlorophenyl)-4-{2S-[3-(4-methoxyphenyl) oxaziridin-2-yl]-3-methylbutane-1-sulfonyl}piperazine A solution of meta-chloroperbenzoic acid (1.2 g) in dichloromethane was dried over magnesium sulfate and then added dropwise to a solution of Intermediate 11 (2.5 g) in dry dichloromethane at −10° C. over 30 min. The mixture was stirred for 2 h, then washed with saturated aqueous sodium bicarbonate solution, water and brine, then dried over MgSO$_4$ and evaporated to give the product (2.50 g, 95%) as viscous oil.

TLC $R_f$ 0.34 (2:1 hexanes/ether).

INTERMEDIATE 13

N-{2S-[4-(4-Chlorophenyl)piperazine-1-sulfonylmethyl]-2-methylpropyl}-hydroxylamine Hydroxylamine hydrochloride (2.0 g) was added to a solution of Intermediate 12 (2.5 g) in methanol (50 ml) at room temperature. The solution was stirred overnight, then evaporated in vacuo and the residue dissolved in water and washed with ether (2×50 ml). The aqueous layer was basified with solid sodium bicarbonate and then extracted with ethyl acetate (2×50 ml) and evaporated to give the crude hydroxylamine (1.2 g), 70% which was used without purification.

TLC $R_f$ 0.20 EtOAc).

EXAMPLE 1

2-Hydroxy-3-[(4-methoxybenzenesulfonyl)methyl]-6-phenylhexanoic Acid

Intermediate 4 (1.443 g) was heated to reflux with 7 M hydrochloric acid (30 ml) for 2 hours. The mixture was then cooled, and extracted with dichloromethane (2×20 ml). The dichloromethane extracts were then reduced to 20 ml, diluted with diethyl ether (100 ml), and extracted with 1 M sodium carbonate solution (2×10 ml). The combined basic extracts were washed with ethyl acetate (10 ml), acidified with 12 M hydrochloric acid, and extracted with dichloromethane (2×15 ml). The dichloromethane extracts were then washed with water (10 ml), dried (MgSO$_4$), and reduced to give the title compound as an off-white solid (0.888 g, 59%).

TLC $R_f$ 0.35 (5% methanol/dichloromethane), MS 410 (M+NH$_4^+$).

EXAMPLE 2

Methyl 3-(4-Methoxybenzenesulfonylmethyl)-2-oxo-6-phenylhexanoate

To a stirred solution of Intermediate 5 (330 mg) in dichloromethane/methanol (7:3; 10 ml) at −78° C. was introduced ozone until the blue colouration persisted. Nitrogen gas was passed through the solution until it was colourless and it was then allowed to warm to RT. Stirring was continued for 30 mins before the solvent was removed in vacuo and the residue purified by silica gel column chromatography, eluting with hexane/ethyl acetate (2:1), to yield the title product as a white solid, (89 mg, 43%).

m.p. 95° C., TLC $R_f$ 0.31 (2:1 hexane/ethyl acetate).

EXAMPLE 3

3-(4-Methoxy-benzenesulfonylmethyl)-2-oxo-6-phenylhexanoic Acid

To a stirred solution of Example 2 (47 mg) in dioxane (5 ml) in an ice-salt bath was added a solution of lithium hydroxide (24 mg) in water (2 ml). Stirring was continued for 90 mins before diluting with water (30 ml) and washing with dichloromethane (2×10 ml). The aqueous layer was acidified (2M HCl) and extracted with ethyl acetate (4×10 ml). The combined ethyl acetate extracts were washed with water (2×10 ml), brine (10 ml) and dried (MgSO$_4$). Filtration and evaporation of the solvent and purification of the residue by silica gel column chromatography eluting with hexane/ethyl acetate/acetic acid (1:1:0.002) yielded the title compound as a colourless oil (30 mg; 67%).

TLC $R_f$ 0.36 (1:1 hexane/ethyl acetate and 0.2% acetic acid), MS 390 (M$^+$).

EXAMPLE 4

N-{1S-[4-(4-Chlorophenyl)piperazine-1-sulfonylmethyl]-2-methylpropyl}-N-hydroxyformamide Intermediate 13 (1.2 g) was stirred in a mixture of THF (50 ml), ethyl formate (2 ml) and triethlamine (1 ml) at reflux for 3 h. The solvent was then evaporated in vacuo and the residue purified by flash column chromatography over silica gel, eluting with 5% methanol in dichloromethane, to give the title compound (0.15 g, 11%) as colourless solid.

TLC $R_f$ 0.37 (5% MeOH/CH$_2$Cl$_2$), MS 290 (MH$^+$).

What is claimed is:

1. A method for treating a condition associated with matrix metalloproteinases or that is mediate by TNFα or enzymes involved in the shedding of L-selectin, CD23, the TNF receptors, IL-1 receptors, or IL-6 receptors, wherein said method comprises the administration of an effective amount a composition comprising a compound of formula (I)

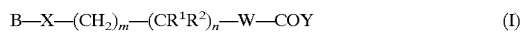

wherein m=0–2;

n=1–2, provided that when m=0, then n=2;

X is S(O)$_{0-2}$;

Y is H;

W is N—OR$^8$;

R$^1$ is H or a substituent (optionally substituted with R$^7$) selected from the group consisting of C$_{1-6}$ alkyl, C$_{2-6}$ alkenyl, aryl, C$_{1-6}$ alkyl-aryl, heteroaryl, C$_{1-6}$ alkyl-heteroaryl, heterocycloalkyl, C$_{1-6}$ alkyl-heterocycloalkyl, cycloalkyl, and C$_{1-6}$ alkyl-cycloalkyl;

R$^2$ is H or C$_{1-6}$ alkyl, provided that (CR$^1$R$^2$)$_n$ is not (CH$_2$)$_n$;

or CR$^1$R$^2$ is a cycloalkyl or heterocycloalkyl ring optionally substituted with R$^7$ or a group (optionally substituted with $R^7$) selected from the group consisting of $C_{1-6}$ alkyl, aryl, $C_{1-6}$ alkyl-aryl, heteroaryl, and $C_{1-6}$ alkyl-heteroaryl;

B is selected from the group consisting of $C_{1-6}$ alkyl-aryl, $C_{1-6}$ alkyl, cycloalkyl, $C_{1-6}$ alkyl-cycloalkyl, cycloalkenyl, heterocycloalkenyl, $C_{1-6}$ alkyl-heteroaryl, heterocycloalkyl, $C_{1-6}$ alkyl-heterocycloalkyl, aryl, and heteroaryl, any of which groups can optionally be substituted by a substituent selected from the group consisting of $R^3$, $C_{1-6}$ alkyl-$R^3$, $C_{2-6}$ alkenyl-$R^3$, aryl (optionally substituted with $R^3$), aryl-$C_{1-6}$ alkyl-$R^3$, $C_{1-6}$ alkyl-aryl (optionally substituted with $R^3$), $C_{1-6}$ alkyl-heteroaryl (optionally substituted with $R^3$), aryl-$C_{2-6}$ alkenyl-$R^5$, heteroaryl (optionally substiatuted with $R^3$), heteroaryl-$C_{1-6}$ alkyl-$R^3$, cycloalkyl (optionally substituted with $R^3$), and heterocycloalkyl (optionally substituted with $R^3$);

$R^3$ is selected from the group consisting of $C_{1-6}$ alkyl, halogen, CN, $NO_2$, $N(R^4)_2$, $OR^4$, $COR^4$, $C(=NOR^6)$ $R^4$, $CO_2R^8$, $CON(R^4)_2$, $NR^4R^5$, $S(O)_{0-2}R^6$, and $SO_2N(R^4)_2$;

$R^4$ is H or a substituent selected from the group consisting of $C_{1-6}$ alkyl, aryl, $C_{1-6}$ alkyl-aryl, heteroaryl, $C_{1-6}$ alkyl-heteroaryl, cycloalkyl, $C_{1-6}$ alkyl-cycloalkyl, heterocycloalkyl, and $C_{1-6}$ alkyl-heterocycloalkyl, wherein said substituent is optionally substituted with $R^6$, $COR^6$, $SO_{0-2}R^6$, $CO_2R^6$, $OR^6$, $CONR^8R^6$, $NR^8R^6$, halogen, CN, $SO_2NR^8R^6$, or $NO_2$, and for each case of $N(R^4)_2$, The $R^4$ groups are the same or different, or $N(R^4)_2$ is heterocycloalkyl optionally substituted with $R^6$, $COR^6$, $SO_{0-2}R^6$, $CO_2R^6$, $OR^6$, $CONR^8R^6$, $NR^8R^6$, halogen, CN, $SO_2NR^8R^6$, or $NO_2$;

$R^5$ is selected from the group consisting of $COR^4$, $CON(R^4)_2$, $CO_2R^6$, and $SO_2R^6$;

$R^6$ is selected from the group consisting of $C_{1-6}$ alkyl, aryl, $C_{1-6}$ alkyl-aryl, heteroaryl, and $C_{1-6}$ alkyl-heteroaryl;

$R^7$ is selected from the group consisting of $OR^4$, $COR^4$, $CO_2R^8$, $CON(R^4)_2$, $NR^4R^5$, $S(O)_{0-2}R^6$, $SO_2N(R^4)_2$, halogen, CN, and cycloimidyl (optionally substituted with $R^8$); and $R^8$ is H or $C_{1-6}$ alkyl;

or a salt, solvate, hydrate, N-oxide or protected amino, protected carboxy, or proteted hydroxamic acid derivative thereof.

2. The method, according to claim 1, wherein $R^1$ is selected from the group consisting of optionally substituted $C_{1-6}$ alkyl, $C_{1-6}$ alkyl-heteroaryl, and $C_{1-6}$ alkyl-heterocycloalkyl; or $CR^1R^2$ forms the said optionally substituted ring.

3. The method, according to claim 1, wherein B is selected from the group consisting of cycloalkyl, heterocycloalkyl, alkyl, and heteroaryl, any of which groups can be optionally substituted by a substituent selected from the group consisting of $R^3$, aryl (optionally substituted with $R^3$), and heteroaryl (optionally substituted with $R^3$).

4. The method, according to claim 1, wherein $R^3$ is $OR^4$ or $COR^4$.

5. The method, according to claim 1, wherein $R^4$ is selected from the group consisting of optionally substituted aryl, $C_{1-6}$ alkyl-aryl, heteroaryl, and $C_{1-6}$ alkyl-heteroaryl.

6. The method, according to claim 1, wherein $R^7$ is selected from the group consisting of $CO_2R^8$, $CON(R^4)_2$, $NR^4R^5$, $S(O)_{0-2}R^6$, $SO_2N(R^4)_2$, and optionally substituted cycloimidyl.

7. A compound of formula (I)

$$B-X-(CH_2)_m-(CR^1R^2)_n-W-COY \quad (I)$$

wherein m=0–2;

n=1–2, provided that when m=0, then n=2;

X is $S(O)_{0-2}$;

Y is H;

W is $N-OR^8$;

$R^1$ is H or a substituent (optionally substituted with $R^7$) selected from the group consisting of $C_{1-6}$ alkyl, $C_{2-6}$ alkenyl, aryl, $C_{1-6}$ alkyl-aryl, heteroaryl, $C_{1-6}$ alkyl-heteroaryl, heterocycloalkyl, $C_{1-6}$ alkyl-heterocycloalkyl, cycloalkyl, and $C_{1-6}$ alkyl-cycloalkyl;

$R^2$ is H or $C_{1-6}$ alkyl, provided that $(CR^1R^2)_n$ is not $(CH_2)_n$;

or $CR^1R^2$ is a cycloalkyl or heterocycloalkyl ring optionally substituted with $R^7$ or a group (optionally substituted with $R^7$) selected from the group consisting of $C_{1-6}$ alkyl, aryl, $C_{1-6}$ alkyl-aryl, heteroaryl, and $C_{1-6}$ alkyl-heteroaryl;

B is selected from the group consisting of $C_{1-6}$ alkyl-aryl, $C_{1-6}$ alkyl, cycloalkyl, $C_{1-6}$ alkyl-cycloalkyl, cycloalkenyl, heterocycloalkenyl, $C_{1-6}$ alkyl-heteroaryl, heterocycloalkyl, $C_{1-6}$ alkyl-heterocycloalkyl, aryl, and heteroaryl, any of which groups can optionally be substituted by a substituent selected from the group consisting of $R^3$, $C_{1-6}$ alkyl-$R^3$, $C_{2-6}$ alkenyl-$R^3$, aryl (optionally substituted with $R^3$), aryl-$C_{1-6}$ alkyl-$R^3$, $C_{1-6}$ alkyl-aryl (optionally substituted with $R^3$), $C_{1-6}$ alkyl-heteroaryl (optionally substituted with $R^3$), aryl-$C_{2-6}$ alkenyl-$R^5$, heteroaryl (optionally substiatuted with $R^3$), heteroaryl-$C_{1-6}$ alkyl-$R^3$, cycloalkyl (optionally substituted with $R^3$), and heterocycloalkyl (optionally substituted with $R^3$);

$R^3$ is selected from the group consisting of $C_{1-6}$ alkyl, halogen, CN, $NO_2$, $N(R^4)_2$, $OR^4$, $COR^4$, $C(=NOR^6)$ $R^4$, $CO_2R^8$, $CON(R^4)_2$, $NR^4R^5$, $S(O)_{0-2}R^6$, and $SO_2N(R^4)_2$;

$R^4$ is H or a substituent selected from the group consisting of $C_{1-6}$ alkyl, aryl, $C_{1-6}$ alkyl-aryl, heteroaryl, $C_{1-6}$ alkyl-heteroaryl, cycloalkyl, $C_{1-6}$ alkyl-cycloalkyl, heterocycloalkyl, and $C_{1-6}$ alkyl-heterocycloalkyl, wherein said substituent is optionally substituted with $R^6$, $COR^6$, $SO_{0-2}R^6$, $CO_2R^6$, $OR^6$, $CONR^8R^6$, $NR^8R^6$, halogen, CN, $SO_2NR^8R^6$, or $NO_2$, and for each case of $N(R^4)_2$, the $R^4$ groups are the same or different, or $N(R^4)_2$ is heterocycloalkyl optionally substituted with $R^6$, $COR^6$, $SO_{0-2}R^6$, $CO_2R^6$, $OR^6$, $CONR^8R^6$, $NR^8R^6$, halogen, CN, $SO_2NR^8R^6$, or $NO_2$;

$R^5$ is selected from the group consisting of $COR^4CON(R^4)_2$, $CO_2R^6$, and $SO_2R^6$;

$R^6$ is selected from the group consisting of $C_{1-6}$ alkyl, aryl, $C_{1-6}$ alkyl-aryl, heteroaryl, and $C_{1-6}$ alkyl-heteroaryl;

$R^7$ is selected from the group consisting of $OR^4$, $COR^4$, $CO_2R^8$, $CON(R^4)_2$, $NR^4R^5$, $S(O)_{0-2}R^6$, $SO_2N(R^4)_2$, halogen, CN, and cycloimidyl (optionally substituted with $R^8$); and $R^8$ is H or $C_{1-6}$ alkyl;

or a salt, solvate, hydrate, N-oxide or protected amino, protected carboxy, or proteted hydroxamic acid derivative thereof.

8. The compound, according to claim 7, wherein X is $SO_2$.

9. A compound, according to claim 7, wherein B is selected from the group consisting of heterocycloalkenyl, heterocycloalkyl or heteroaryl.

10. A compound, according to claim 7, wherein B is selected from the group consisting of azetidinyl, pyrrolidinyl, tetrahydrofuranyl, piperidinyl, indolinyl, tetrahydroquinolinyl, dihydropyranyl, furanyl, thiophenyl, pyridyl, indolyl and quinolyl.

11. The compound, according to claim 7, which is N-{1S-[4-(4-chlorophenyl)piperazine-1-sulfonylmethyl]-2-methylpropyl}-N-hydroxyformamide.

12. The compound, according to claim 11, wherein said compound is in the form of a single enantiomer or diastereomer.

13. A pharmaceutical composition for use in therapy, comprising a compound as defined in claim 7, and a pharmaceutically-acceptable diluent or carrier.

14. A method for the treatment of tumor growth, angiogenesis, tumor invasion and spread, metastases, malignant acites, malignant pleural effusion, osteoarthritis, rheumatoid arthritis, osteoporosis, periodontitis, gingivitis, surgical wound healing, inflammatory diseases, graft-versus-host reactions, hemorrhage, corneal ulceration, chronic ulcers, retinopathy, ocular inflammation, keratoconus, or inflammation, wherein said method comprises the administration of a composition comprising a compound of claim 1.

15. A method for reducing the activity of matrix metalloproteases comprising the administration of an effective amount of a composition according to claim 13.

* * * * *

UNITED STATES PATENT AND TRADEMARK OFFICE
CERTIFICATE OF CORRECTION

PATENT NO. : 6,100,266  
DATED : August 8, 2000  
INVENTOR(S) : John Gary Montana, Andrew Douglas Baxter, David Alan Owen Page 1 of 1

It is certified that error appears in the above-identified patent and that said Letters Patent is hereby corrected as shown below:

<u>Column 16, claim 7,</u>  
Lines 62-63, "$COR^4CON(R^4)_2$," should read -- $COR^4, CON(R^4)_2$, --.

Signed and Sealed this

Twenty-sixth Day of February, 2002

Attest:

JAMES E. ROGAN  
*Attesting Officer*  *Director of the United States Patent and Trademark Office*